United States Patent [19]

Wright et al.

[11] Patent Number: 5,189,210

[45] Date of Patent: Feb. 23, 1993

[54] PROCESS FOR THE PREPARATION OF 3- AND/OR 5-SUBSTITUTED ANTHRANILIC ACIDS

[75] Inventors: Terry L. Wright, Oakland, Calif.; Jon A. Orvik, Midland, Mich.

[73] Assignee: DowElanco, Indianapolis, Ind.

[21] Appl. No.: 876,651

[22] Filed: Apr. 30, 1992

[51] Int. Cl.$^5$ ............................................. C07C 51/16
[52] U.S. Cl. .................................................... 562/418
[58] Field of Search ......................................... 562/418

Primary Examiner—Michael L. Shippen
Attorney, Agent, or Firm—Craig E. Mixan; Kenneth L. Loertscher

[57] ABSTRACT

Anthranilic acids substituted in the 3- and/or 5-position are valuable intermediates for the production of agricultural chemicals. These substituted anthranilic acids can be obtained in good yield without undesirable isomeric byproducts by the oxidative ring-opening of dihydroquinolin-4-ones or quinolin-2,4-diones with t-butyl hydroperoxide in the presence of a base.

6 Claims, No Drawings

PROCESS FOR THE PREPARATION OF 3- AND/OR 5-SUBSTITUTED ANTHRANILIC ACIDS

FIELD OF THE INVENTION

The present invention concerns a process for preparing 3- and/or 5-substituted anthranilic acids from 6- and/or 8-substituted quinolin-4-one derivatives. More particularly, the present invention concerns a process for preparing 3- and/or 5-substituted anthranilic acids by the basic tert-butyl hydroperoxide oxidation of 6- and/or 8-substituted 2,3-dihydroquinolin-4-ones and of 6- and/or 8-substituted quinolin-2,4-diones.

BACKGROUND OF THE INVENTION

Substituted anthranilic acid derivatives are useful intermediates in the manufacturing of a variety of chemical products including agricultural chemicals; see, for example, U.S. Pat. No. 4,954,163.

The direct electrophilic substitution of anthranilates to 3- and/or 5-substituted analogs is often not very successful because of the mixtures produced. Chlorination of methyl anthranilate, for example, gives mixtures of 5-chloroanthranilate and 3-chloroanthranilate along with substantial amounts of dichlorination.

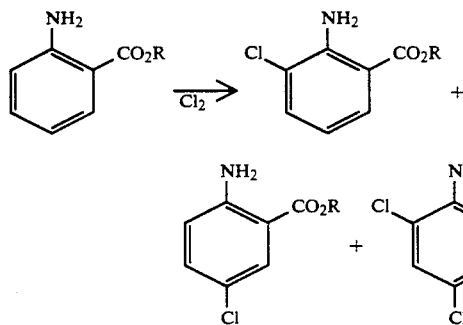

Because of the unpredictability with respect to electrophilic substitutions, other approaches to substituted anthranilates are usually advocated. For example, U.S. Pat. No. 4,306,074 discloses the preparation of a mixture of alkyl 3-chloroanthranilate and alkyl 6-chloroanthranilate in a 3:1 ratio from 3-chlorophthalic anhydride by amination, Hofmann degradation and esterification.

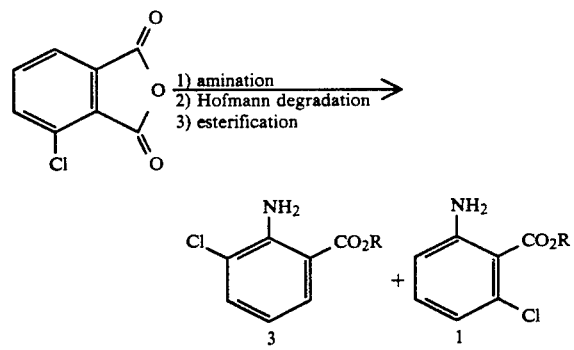

Despite three discrete steps, a mixture is still produced.

In U.S. Pat. No. 4,310,677, alkyl anthranilates are prepared by reacting an isatin with an alcohol and hydrogen peroxide in the presence of an alkali metal alkoxide.

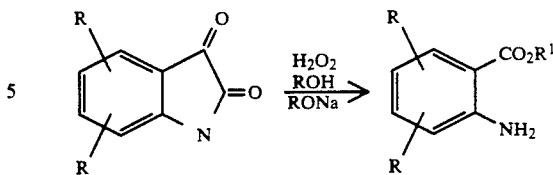

However, the isatins required for this approach are often very difficult to prepare.

Therefore, it is desirable to have a process for preparing anthranilic acids, particularly 3- and/or 5-substituted anthranilic acids, in good yield and free of isomeric byproducts from readily available starting materials.

SUMMARY OF THE INVENTION

We have now found that 2,3-dihydroquinolin-4-ones and quinolin-2,4-diones, which can be easily prepared from readily available starting materials, can be converted to anthranilic acids by oxidation with tert-butyl hydroperoxide under basic conditions. The products are obtained in good yield, free of isomeric byproducts. Therefore, the present invention concerns a process for the preparation of an anthranilic acid of formula I

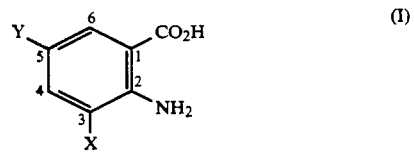

wherein
X and Y independently represent H,
halogen, $CF_3$ or a $C_1$-$C_4$ alkyl group,
which is characterized by contacting a quinolin-4-one of formula II

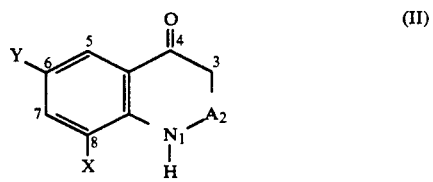

wherein
A represents

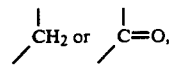

and
X and Y are as previously defined,
with t-butyl hydroperoxide in an inert organic solvent in the presence of a base.

DETAILED DESCRIPTION OF THE INVENTION

As used herein, the term "alkyl" when used alone or incorporated into terms like "alkoxide" and "alcohol" is meant to designate straight or branched, saturated alkyl groups of from 1 to 4 carbon atoms. The terms "halogen," "halo" and "halide" are meant to refer to fluorine, chlorine and bromine.

The 6- and/or 8-substituted 2,3-dihydroquinolin-4-one and quinolin-2,4-dione starting materials of formula II are conveniently prepared from 2- and/or 4-substituted anilines. For example, a substituted aniline can be reacted with acrylic acid to form an anilinopropionic acid which can be cyclized in polyphosphoric acid (PPA) to give the corresponding 2,3-dihydroquinolin-4-one.

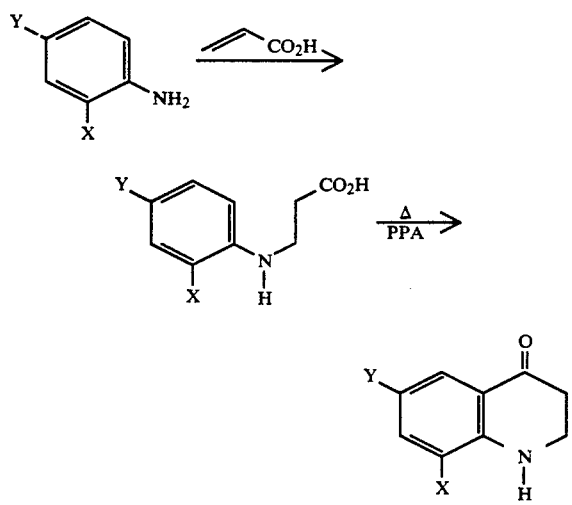

Similarly, a substituted aniline can be reacted with ethyl malonyl chloride to form a malonyl carboxamide which can be hydrolyzed and cyclized in PPA to give the corresponding quinolin-2,4-dione.

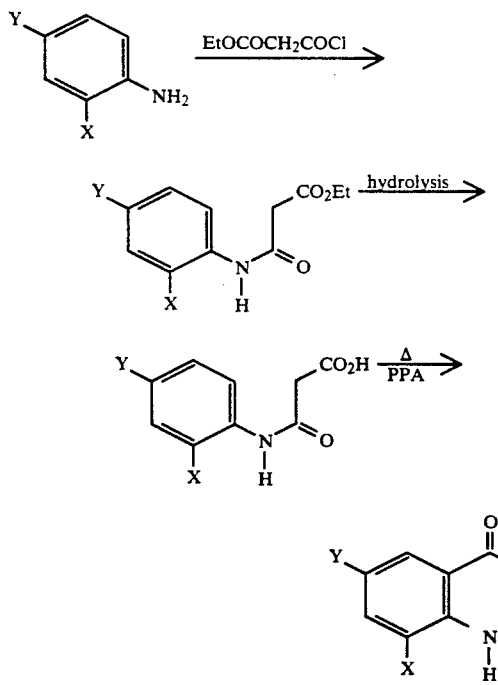

These preparations, particularly the cyclizations, are considerably more facile than those of the corresponding isatins. Preferred starting materials are those in which Y is hydrogen and X is halogen, particularly F and Cl. In the most preferred embodiments, A represents —$CH_2$—.

Tert-butyl hydroperoxide is commercially available in concentrations of from 70 to 90 percent in admixture with t-butyl alcohol and water. These materials are suitable for use as supplied. If, however, dry conditions are desired, anhydrous organic solutions can be prepared by employing phase separation and azeotropic distillation techniques; see K. B. Sharpless et al., Aldrichimica Acta 12, 63 (1979).

To achieve complete oxidation, at least 3 equivalents of t-butyl hydroperoxide are required for each equivalent of quinolin-2,4-dione (A is C=O) and at least 5 equivalents of t-butyl hydroperoxide are required for each equivalent of dihydroquinolin-4-one (A is $CH_2$). The use of larger excesses of hydroperoxide is often recommended.

The reaction is ineffective under acidic or neutral conditions and must be conducted in the presence of a base. Suitable bases include the alkali metal and alkaline earth hydroxides, carbonates and alkoxides, particularly those of sodium and potassium. In order to achieve complete conversion, at least 3 equivalents of base are required for each equivalent of quinolin-2,4-dione (A is C=O) and at least 5 equivalents of base are required for each equivalent of dihydroquinolin-4-one (A is $CH_2$). In the absence of a much larger than required excess of hydroperoxide, it is recommended to use equimolar amounts of base and hydroperoxide.

The reaction can be conducted in any solvent which is inert to the reaction conditions and in which the reactants are at least partially soluble. Preferred solvents are alcohols and water which are particularly well suited for using the t-butyl hydroperoxide as it is supplied. The most preferred solvent is water.

The reaction typically takes place at temperatures between 50° and 120° C., most preferably between 60° and 95° C., and is most conveniently carried out at the reflux temperature of the mixture.

The process is usually conducted by introducing the quinolin-4-one, the t-butyl hydroperoxide, the base and the solvent into the reaction vessel and heating the mixture until the reaction is completed, usually in from 1 to 5 days. The anthranilic acid product is then isolated by conventional techniques such as extraction or precipitation.

The following examples are meant to illustrate the invention and should not be construed as a limitation on the scope of the invention.

EXAMPLE A

Preparation of 8-Fluoro-2,3-dihydroquinolin-4-one Starting Material

1. 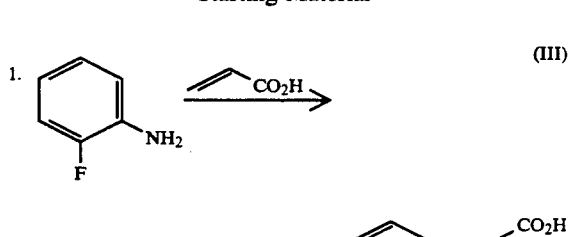

(III)

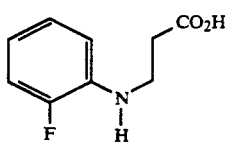

1a. 2-Fluoroaniline (50 grams (g), 0.45 mol) and acrylic acid (35 g, 0.49 mol) were slowly added to 500 milliliters (mL) of acetonitrile. The resulting solution was heated to reflux for 18 hours (hr). The solution was cooled and evaporated in vacuo. The residue was redissolved in a 10 percent solution of sodium hydroxide and then extracted with methylene chloride. The aqueous phase was separated and acidified to pH 3. The resulting precipitate was filtered and dried to yield 42 g of white solid melting at 100°–101° C.

1b. 2-Fluoroaniline (111 g, 1.0 mol) and acrylic acid (80 g, 1.11 mol) were added to 600 mL of water and the resulting mixture was heated to reflux for 48 hr. The 2-phase mixture was cooled, whereupon one phase solidified. The solids were broken up with a spatula and collected by filtration. The solids were washed several times with water and dried to yield 189 g (92 percent) of compound III (melting point: 100°–101° C.).

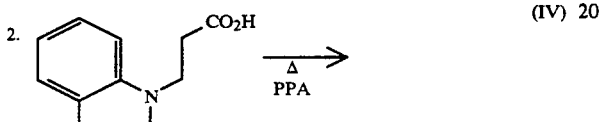

Polyphosphoric acid (80 g) was heated to 130° C., and 3-(N-(2-fluorophenyl))aminopropionic acid (6.0 g) was added to the rapidly stirred solution. The reaction was followed by high pressure liquid chromatography (HPLC) and the reaction was judged complete in about 45 minutes (min). The solution was quenched in ice water (200 g), and the resulting solution was acidified to pH 5. The solid that precipitated was collected by filtration and dried to yield 4.2 g of product. The NMR spectrum and melting point (125°–127° C.) were consistent with compound IV.

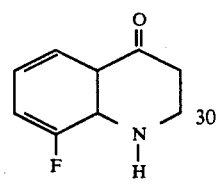

EXAMPLE B

Preparation of 8-Fluoroquinolin-2,4-dione Starting Material

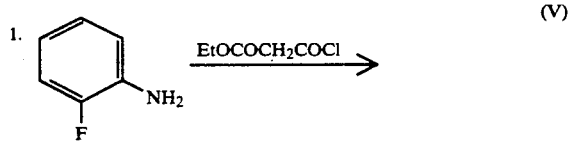

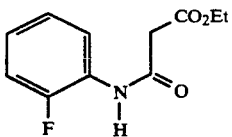

To a solution of 14.7 g (0.1 mol) of 2-fluoroaniline and 15 g (0.15 mol) of triethylamine in methylene chloride was added 20 g (0.13 mol) of ethyl malonyl chloride over 30 min. The mixture was stirred for 2 hr at ambient temperature and was quenched in water. The organic phase was separated, dried with sodium sulfate and concentrated to give a brown oil, the nmr spectrum of which was consistent with the structure of V.

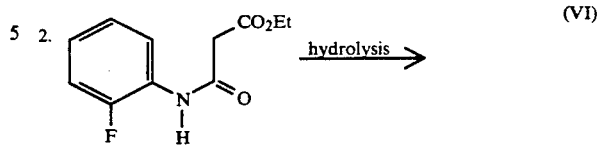

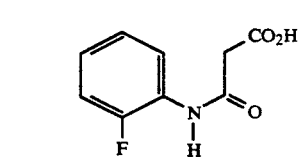

Compound V (2 g) was stirred at 70° C. with NaOH (2 g) in 20 mL of water. The initially heterogeneous mixture became homogeneous during the course of about 1 hr. The clear solution was neutralized with HCl to give 1.2 g of VI as white needles.

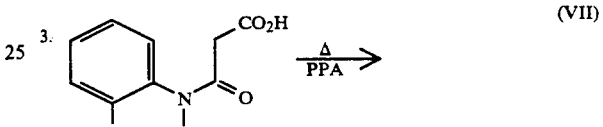

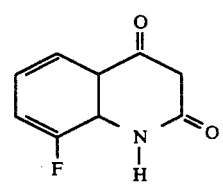

Compound VI (1 g) was heated to 140° C. with stirring in 10 g of polyphosphoric acid (PPA). After 1 hr, the reaction mixture was poured into water and the resulting precipitate was collected and dried to give 0.7 g of VII.

$^1$H NMR (dmso-d$_6$): δ11.5 (s, 1H), 11.3 (s, 1H), 7.6 (d, 1H), 7.4 (m, 1H), 7.2 (m, 1H) and 5.8 (s, 1H).

EXAMPLE 1

Preparation of 3-Fluoroanthranilic Acid from 8-Fluoroquinolin-2,4-dione

A solution of 0.1 g (0.6 mmol) of 8-fluoroquinolin-2,4-dione, 0.1 g (7.8 mmol) of 70 percent t-butyl hydroperoxide, 0.2 g of 25 percent sodium methoxide in methanol and an additional 2 mL of methanol was heated at 75° C. with stirring for 48 hr. An additional 0.2 g of t-butyl hydroperoxide and 0.5 mL of 25 percent sodium methoxide in methanol were added and heating was continued for 24 more hr. The reaction mixture was cooled, poured into water, and neutralized with acetic acid. The mixture was extracted with methylene chloride and the organic phase was collected. Evaporation of the solvent gave 0.35 g (40 percent yield) of 3-fluoroanthranilic acid, mp 172° C.

EXAMPLE 2

Preparation of 3-Fluoroanthranilic Acid from 8-Fluoro-2,3-dihydroquinolin-4-one

A. A solution of 0.25 g (1.5 mmol) of 8-fluoro-2,3-dihydroquinolin-4-one, 0.8 g (6.2 mmol) of 70 percent t-butyl hydroperoxide, 2 mL of 25 percent sodium methoxide in methanol and 3 mL of methanol were stirred at 75° C. for 72 hr. An additional 1 mL of 70 percent t-butyl hydroperoxide and 2 mL of 25 percent sodium methoxide in methanol were added and heating was continued for 72 more hr. The reaction mixture was cooled, poured into water and neutralized with acetic acid. The mixture was extracted with methylene chloride and the organic phase was collected. Evaporation of the solvent gave 0.12 g (51 percent yield) of 3-fluoroanthranilic acid, identical in all respects to an authentic sample.

B. A solution of 100 mL of methanol, 5.0 g (0.03 mol) of 8-fluoro-2,3-dihydroquinolin-4-one and 40 g of 25 percent sodium methoxide in methanol was stirred for several minutes at ambient temperature and 18 g (0.18 mol) of 90 percent t-butyl hydroperoxide were added over 2 min. The reaction mixture was heated to reflux and after 48 hr an additional 15 g of t-butyl hydroperoxide was added. After heating for an additional 48 hr, the reaction mixture was cooled and the pH was adjusted to about 3 with concentrated HCl. Most of the alcohol was evaporated under reduced pressure and the residue was slurried with water. Crude 3-fluoroanthranilic acid (2.8 g) was collected by filtration. Recrystallization from methanol gave 1.9 g of crystals.

C. To a solution of 4.4 g (0.11 mol) of NaOH and 11 g (0.11 mol) of t-butyl hydroperoxide in 40 mL of water was added 3.0 g (0.018 mol) of 8-fluoro-2,3-dihydroquinolin-4-one. The mixture was heated to 90° C. for 48 hr at which time an additional 11 g of t-butyl hydroperoxide were added and heating was continued for an additional 72 hr. After cooling, most of the reaction liquid was evaporated under reduced pressure and the residue was diluted with 100 mL of water and acidified to a pH of about 5. The precipitated 3-fluoroanthranilic acid was collected by filtration and dried to give 1.4 g (55 percent yield) of solid.

$^1$H NMR (dmso-d$_6$): δ7.65 (d, 1H), 7.15 (t, 1H) and 6.45 (m, 1H).

What is claimed is:

1. A process for the preparation of an anthranilic acid of formula I:

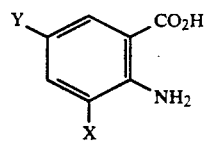

wherein
X and Y independently represent H, halogen, CF$_3$ or a C$_1$–C$_4$ alkyl group,
which comprises contacting a quinolin-4-one of formula II

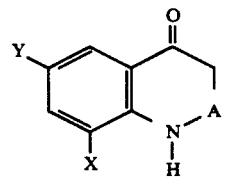

wherein
A represents

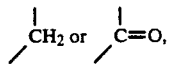

and
X and Y are as previously defined,
with t-butyl hydroperoxide in an inert organic solvent in the presence of a base.

2. The process of claim 1 in which Y is hydrogen and X is halogen.

3. The process of claim 1 in which A is —CH$_2$—.

4. The process of claim 1 in which Y is hydrogen, X is F or Cl and A is —CH$_2$—.

5. The process of claim 1 in which the inert organic solvent is an alcohol of from 1 to 4 carbon atoms or water.

6. The process of claim 1 in which the base is an alkali metal or alkaline earth metal hydroxide, carbonate or alkoxide.

* * * * *